United States Patent [19]

Langer et al.

[11] 4,361,714
[45] Nov. 30, 1982

[54] PREPARATION OF LINEAR OLEFIN PRODUCTS

[75] Inventors: Arthur W. Langer, Watchung; John J. Steger, Scotch Plains; Terry J. Burkhardt, Cranford, all of N.J.

[73] Assignee: Exxon Research and Engineering Co., Florham Park, N.J.

[21] Appl. No.: 330,480

[22] Filed: Dec. 14, 1981

[51] Int. Cl.³ ............................................. C07C 2/02
[52] U.S. Cl. ................................. 585/521; 526/159; 526/163; 585/511; 585/523; 252/431 R; 252/441
[58] Field of Search ............... 585/512, 513, 521, 523, 585/525, 527; 526/159, 163

[56] References Cited

U.S. PATENT DOCUMENTS

| | | | |
|---|---|---|---|
| 2,907,805 | 10/1959 | Bestian et al. | 585/524 |
| 2,993,942 | 7/1961 | White et al. | 585/524 |
| 3,441,630 | 4/1969 | Langer, Jr. et al. | 585/524 |
| 3,662,021 | 5/1972 | Langer, Jr. | 585/524 |

Primary Examiner—Delbert E. Gantz
Assistant Examiner—A. Pal
Attorney, Agent, or Firm—Richard E. Nanfeldt

[57] ABSTRACT

A process for preparing linear alpha olefins and waxes having a total product $\overline{M}_n$ in the range 200 to 700 which includes polymerizing an ethylene-containing gas in the presence of the reaction product of a zirconium halide with $R_2Zn$, wherein R is an alkyl group having about 1 to about 20 carbon atoms, in the presence of a diluent at a temperature of about 50° to 200° C. and an ethylene pressure above about 3.5 MPa, wherein the $\overline{M}_n$ of said reaction product is controlled by the molar ratio of said $R_2Zn/ZrCl_4$, said molar ratio being less than about 1.

7 Claims, No Drawings

PREPARATION OF LINEAR OLEFIN PRODUCTS

FIELD OF THE INVENTION

This invention relates to an improved process for preparing linear olefins and waxes, particularly linear alpha olefins. More particularly, this invention relates to an improved process for polymerizing ethylene to obtain linear olefins and waxes having a number average molecular weight ($\overline{M}_n$) ranging from about 200 to 700.

Still more particularly, this invention relates to an improved process for polymerizing ethylene to obtain a product comprising at least 90 mole percent linear alpha olefins and waxes having a number average molecular weight greater than about 250, and especially greater than about 280.

PRIOR ART

It has been shown in the prior art (U.S. Pat. Nos. 2,993,942 and 2,907,805) that hydrocarbon lubricating oils having a molecular weight in the range of 80 to 2000 could be prepared by polymerizing ethylene with controlled catalyst compositions, diluents and under controlled temperatures. The catalyst consisted of a transition metal halide and a halogenated aluminum alkyl compound. It has also been found that increased oil yields, catalyst reactivity and improved molecular weight control could be obtained by the addition of a minor amount of a lower alkanol, as a catalyst modifier to the reaction system. Both the modified and unmodified systems described above resulted, under the conditions in the reaction, in the production of major portions of olefins other than linear alpha olefin products, particularly Type II (RCH=CHR), Type III

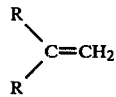

and Type IV

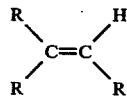

olefins.

Ethylene oligomerization to linear alpha olefins was discovered by one of the inventors of the instant invention, Arthur Langer, who used substantially soluble catalysts comprising tetravalent titanium halides and alkyl aluminum halides under controlled reaction conditions, as described in U.S. Pat. Nos. 3,441,360; 3,647,912; 3,655,812; and 3,662,021. Other Ziegler-type alkyl metal cocatalysts were not useful for oligomerization because they reduced the titanium compound to the heterogeneous Ziegler catalyst which produced high molecular weight polyethylene.

In this invention, it has been discovered that dialkyl zinc compounds are surprisingly effective cocatalysts for ethylene oligomerization when used in combination with zirconium halides, preferably $ZrCl_4$. It was further discovered that the total oligomer product molecular weight increased with decreasing ratio of $R_2Zn/ZrCl_4$. This is contrary to the teachings of Ziegler who showed that polyethylene molecular weight increased with increasing ratio of cocatalyst/catalyst, as described in Belgium Pat. No. 540,459 and Raff and Doak, Crystalline Olefin Polymers I, Interscience, 1965, p. 372.

Langer has also disclosed an oligomerization catalyst containing a zirconium tetrahalide and alkyl aluminum chloride cocatalyst, as described in U.S. Ser. No. 105,027. However, there was no disclosure or teaching that other alkyl metal cocatalysts could be used because it was known that other cocatalysts produced polyethylene rather than low molecular weight linear alpha olefins when used in combination with $TiCl_4$.

The new catalysts of the instant invention are especially attractive for making linear alpha olefin wax because higher molecular weights can be attained than using the zirconium catalysts/alkyl aluminum chloride cocatalysts known in the art when compared under the same conditions and optimum proportions. Thus, waxes having an $\overline{M}_n > 250$, and preferably $>280$, are readily made with the new catalysts compared to 230-270 made with $R_2AlCl/ZrCl_4$ or 3-4 $RAlCl_2/1R_2AlCl/1Zr(OR)_4$ catalysts. The molecular weights are calculated from a straight line portion of log mole fraction vs. carbon number between $C_{10}$ and $C_{22}$ (selected for analytical accuracy) based on a Flory distribution ($\overline{M}_w/\overline{M}_n = 2$). In addition to higher $\overline{M}_n$, which increases selectivity to wax, the new catalysts also give very high activities, high purity, linear alpha olefins and a low yield of polyethylene by-product.

SUMMARY OF THE INVENTION

In accordance with this invention, therefore, an improved process for preparing linear olefins, particularly linear alpha olefins and waxes, is provided which comprises polymerizing ethylene or an ethylene-containing gas in the presence of a catalyst comprising the reaction product of a zirconium halide with a dialkyl zinc compound, conducting the polymerization reaction in the presence of a suitable hydrocarbon diluent or a higher olefin fraction such as $C_{22}$–$C_{28}$ at temperatures of about 50° to about 200° C. and ethylene pressures above about 3.5 to about 10.5 MPa for residence times of about 2 to about 60 minutes.

The reaction can be terminated either by removing the ethylene-containing gas, thereby stopping the polymerization or, by adding a polymerization catalyst killing agent, thereby stopping the polymerization activity of the catalyst.

Some typical polymerization killing agents are water, alcohols, (mono- and poly-hydroxylic, cyclic and acyclic, aliphatic and aromatic); carboxylic acids; phenols, etc. The organic compounds which can be used are those having from 1 to 15 carbon atoms, the lower carbon number, inexpensive compounds being preferred. Thus, alcohols and acids having from 1 to 8 carbons are preferred, with 1 to 4 carbons being most preferred. Examples of the most preferred killing agents include water, methanol, ethanol, isopropanol, t-butanol and ethylene glycol, glycol monoalkylethers and the like.

The catalyst is a complex reaction product which is obtained by partially reacting a tetravalent zirconium halide with a diorganozinc compound having the formula $R_2Zn$, wherein R is alkyl, cycloalkyl or aralkyl, preferably containing 1 to 20 carbon atoms, for example, methyl, ethyl, isobutyl, cyclohexyl, benzyl, etc. The preferred zirconium halide catalyst component is a Zr metal compound having a valency of 4, and may be represented by the formula: $ZrX_aA_b$, wherein $a = 3$ or 4, b=1 or 0 and a+b=4, X=Cl or Br and A is Cl, Br, I, OR or OOCR. The most preferred zirconium halide component of this invention is ZrCl$_4$ or ZrBr$_4$.

It has been surprisingly found that when one employs a catalyst system comprising R$_2$Zn, wherein R is an alkyl group having about 1 to 20 carbon atoms, preferably 1 to 5, and most preferably ethyl, and ZrCl$_4$ for the polymerization of ethylene, the $\overline{M}_n$ of the formed ethylene oligomer increases as the molar ratio of R$_2$Zn/ZrCl$_4$ decreases, wherein the molar ratio of R$_2$Zn/ZrCl$_4$ is less than about 1/1, more preferably less than about 0.5/1 and most preferably about 0.1/1 to 0.5/1.

Ethylene is unique in the instant invention in that other olefins do not respond to give linear alpha olefins. Therefore, it is desirable to use essentially pure ethylene or mixtures of ethylene with inert gases as the feed for the process of this invention. Ethylene feeds containing minor amounts of other olefins may be used provided that the extent of copolymerization does not decrease product linearity below 90 percent.

Polymerization diluent is not a critical feature of this invention. The usable diluents are inert hydrocarbons having about 5 to about 30 carbon atoms and haloaromatic solvents, as well as aliphatics and naphthenics. Less preferred solvents are halogenated aliphatic compounds which, while capable of being employed in the process of preparing linear alpha olefins, require the utilization of higher pressures to achieve average molecular weights of the same order as the preferred solvents. The preferred diluents include hydrocarbon solvents, higher olefin product fractions such as C$_{22}$–C$_{28}$, or C$_{20}$+ bottoms, aromatics such as benzene, toluene, xylene tetrahydronaphthalene, etc., aliphatics such as pentane, heptane, isooctane, etc., and naphthenes such as cyclohexane, methylcyclohexane, decahydronaphthalene, etc. The saturated hydrocarbons are most preferred.

The prior art obtained highly branched olefins (60%) when using the soluble titanium catalysts at pressures of 7 to 30 psig., e.g., British Pat. No. 974,577. Ethylene pressures of the instant invention above 3.5 MPa are essential for making linear olefins in high selectivities. Although some variations are permitted, depending upon the catalyst composition, diluent and temperature, the preferred pressures are above about 5.5 to about 10.5 MPa in order to produce commercially attractive yields (at least above 5 weight percent and preferably above 10 weight percent olefins in the reactor effluent) of linear alpha olefins having a purity greater than about 90 mole percent. At very high ethylene pressures, the process may become uneconomical because of the equipment requirements and ethylene recycle. Nevertheless, higher pressures tend to increase the selectivity of the reaction to linear alpha olefins.

The catalyst of this invention enables the process for making linear alpha olefins to be carried out at temperatures of about 50° to about 200° C., preferably between about 100° C. and about 150° C. The selection of a particular temperature will permit control of the number average molecular weight of the wax product. With these zirconium catalysts, temperatures as high as about 200° C. can be used without making excessive amounts of polyethylene. However, the high temperatures cause product isomerization and require higher ethylene pressures to prevent copolymerization, which makes them less attractive. The preferred temperatures to obtain high purity linear alpha olefins with zirconium tetrachloride catalysts are between about 50° to about 200° C. and more preferably between about 75° to about 150° C. to obtain total product $\overline{M}_n$ greater than 250.

Reaction times are not particularly critical when operating under the preferred conditions and they will normally be in the range of 0.1 to 5 hours to obtain product concentrations greater than 5 percent by weight in the diluent. The process may be carried out in batch or continuous operation. However, high product purity and high concentration are achieved most easily in batch reactions or in continuous systems operating under essentially plug flow conditions. A reactor may consist of a long pipe through which the diluent and catalyst flow with ethylene being introduced at many points along the pipe to maintain the desired ethylene concentration. In such a system monomer concentration need not be constant but may be controlled differently in different sections of the reactor to achieve the best balance of activity, molecular weight and product purity. Stirred tank reactors may be operated in series to approach plug flow.

After the catalyst has been effectively neutralized, the residues may be removed from the products in any conventional way, such as washing with water or aqueous caustic, dilute aqueous acid, adsorption, ion exchange resins, etc. If the catalyst has been neutralized according to this invention, the products may be distilled directly from the catalyst residues without decreasing product purity. However, it is preferred to remove the residues before distillation in order to minimize deposits in the distillation towers.

Based on the teachings of this invention to destroy polymerization activity to permit isolation of greater than 90 mole percent pure linear alpha olefins, it is clearly within the scope of the invention to accomplish the same results by alternatives such as rapid solvent extraction of solid adsorption techniques, particularly if these are used before all of the ethylene has been flashed. However, such techniques are generally less effective than the preferred neutralization procedure.

The following examples are submitted in order to more particularly point out applicant's invention, but are not to be construed as limitations on the scope of the instant invention as described in the appended claims.

EXAMPLE 1

Ethylene oligomerizations were carried out in a 1-liter, stirred autoclave at 130° C. in 500 ml. n-heptane solvent. Commercial grade anhydrous ZrCl$_4$ was purified by sublimation and the powdered solid was stored under dry nitrogen. Catalyst, 5 g.n-C$_{11}$H$_{24}$ and 480 ml. n-heptane were charged to the evacuated autoclave under a dry nitrogen atmosphere. The system was heated to 100° to 110° C. while pressuring to about 6.2 MPa ethylene. The Et$_2$Zn in 20 ml. n-heptane was then pressured into the reactor from a pressure vessel using ethylene, and the reactor was quickly brought to 130° C. to 7 MPa. Ethylene was fed continuously to maintain 7 MPa.

Analytical samples were pressured directly into an alcoholic-NaOH quench in toluene, heated to 100° C., dried over K$_2$CO$_3$ and the clear solution was analyzed by gas chromatography. The number average molecular weight ($\overline{M}_n$) was determined from the slope of a plot of log mole fraction vs. carbon number for the C$_{12-20}$ olefins based on the Flory distribution (P. J. Flory, J. Am. Chem. Soc. 58, 1877 (1936); A. W. Langer, Jr., J. Macromol. Sci.-Chem., A4(4), 775, 1970). Total product yield ($C_4+$) was calculated from the $C_{10}/C_{11}$ weight ratio (corrected for volatility losses) and the theoretical percent of $C_{10}$ in a Flory distribution of the observed $\overline{M}_n$. Product purity is the percent linear alpha olefin in the $C_{12-20}$ fraction. In these oligomerization products, the purity decreases with increasing carbon number due to a greater probability for copolymerization.

TABLE I

| Run | $Et_2Zn$ mmol | $ZrCl_4$ mmmol | $C_2H_4$ MPa | Time min. | Rate g/g$ZrCl_4$/hr. | $\overline{M}_n$ | % Purity |
|---|---|---|---|---|---|---|---|
| A | 0.05 | 0.3 | 5.5 | 30 | 1200 | 283 | 99.4 |
| B | 0.05 | 0.3 | 7.0 | 30 | 5100 | 303 | 99.2 |
| C | 0.05 | 0.3 | 7.0 | 15 | 3700 | 303 | 99.2 |

A comparison of Runs A and B (Table I) shows that both activity and molecular weight increased with increasing ethylene pressure from 5.5 to 7 MPa. Run length did not significantly affect molecular weight (Runs B and C).

EXAMPLE 2

The procedure of Example 1 was followed except that the $Et_2Zn$ was added to the reactor at about 50° C. together with the $ZrCl_4$ slurry. The reactor was evacuated, the temperature was increased to 100° to 110° C. in 7 to 15 min., ethylene was added rapidly to reach 7 MPa at 130° C. and ethylene was added continuously to maintain 7 MPa and 130° C. Control runs using $Et_2AlCl$ (DEAC) are also shown in Table II.

TABLE II

| Run | $Et_2Zn$ mmol | $ZrCl_4$ mmmol | Zn/Zr | Time min. | Rate g/g$ZrCl_4$/hr. | $\overline{M}_n$ | % Purity |
|---|---|---|---|---|---|---|---|
| D | 0.32 | 0.08 | 4.0 | 30 | 6,300 | 228 | 99.1 |
| E | 0.08 | 0.16 | 0.50 | 15 | 5,300 | 261 | 99.8 |
| F | 0.08 | 0.32 | 0.25 | 15 | 6,800 | 285 | 99.1 |
| Controls DEAC | | | Al/Zr | | | | |
| G[a] | 0.40 | 0.10 | 4.0 | 15 | 32,000 | 150 | 95.5 |
| H[a] | 0.10 | 0.20 | 0.5 | 15 | 17,000 | 215 | 96.3 |
| I | 0.06 | 0.24 | 0.25 | 15 | 6,000 | 224 | 99.9 |

[a] 120° C. polymerization temperature instead of 130° C.

The use of $Et_2Zn$ cocatalyst gave much higher molecular weight products than the corresponding control runs using DEAC. These higher molecular weight product distributions are greatly preferred for a wax process because they yield substantially higher selectivities to wax. For example, the highest molecular weight obtained in the DEAC control runs (224 $\overline{M}_n$) yielded only 35 weight percent selectivity to $C_{30}+$ wax. In contrast, $Et_2Zn$ (285 $\overline{M}_n$) yielded 50 percent selectivity under the same conditions.

The most surprising result was that product molecular weight increased with decreasing ratio of cocatalyst/catalyst, especially below 1/1. This is directly contrary to the teachings of Ziegler and others for making polyethylene.

EXAMPLE 3

Ever since the discoveries by Ziegler and his coworkers, it has been known that nearly all Group I-III alkyl metal compounds are effective cocatalysts for polymerizing ethylene or plastics-range, high molecular weight polyethylene, when used in combination with Group IV-VI and VIII transition metal compounds. However, this is clearly not the case for the oligomerization of ethylene to linear alpha olefin liquids and waxes. For oligomerization of ethylene, only Group IV transition metal chlorides, and compounds which are convertible into chlorides by exchange of ligands with chloroaluminum compounds, have been effective only with alkyl aluminum chlorides. Trialkyl aluminum and other alkyl metals are generally not effective for oligomerization because they produce Ziegler polyethylene by-product in large amounts which causes severe reactor fouling and adversely affects economics.

Table III shows the results obtained using the most useful Group I-III alkyl metal cocatalysts for making Ziegler polyethylene (DEAC was discussed in Example 2).

TABLE III

| Control Runs | Cocatalysts Alkyl | mmol | $ZrCl_4$ mmol | °C. | Time min. | Olig. Rate | $\overline{M}_n$ | % P.E.[a] |
|---|---|---|---|---|---|---|---|---|
| J | BuLi | 0.08 | 0.24 | 130 | 20 | 0 | — | — |
| | | +0.08 | | | 30 | 1000 | 172 | 7.4 |
| K | n + s-$Bu_2Mg$ | 0.06 | 0.24 | 130 | 33 | 0 | — | — |
| | | +0.03 | | | 15[b] | 2200 | 198 | 44.5 |
| L | $EtAlCl_2$ | 0.08 | 0.32 | 130 | 24 | 0 | — | — |
| | | +0.08 | | | 26 | 0 | — | — |
| M | $Et_3Al$ | 0.05 | 0.1 | 120-7 | 10[b] | 18800 | 199 | 4.8 |

[a] Polyethylene (boiling n-heptane insolubles), percent of oligomer yield.
[b] Run terminated by polyethylene fouling In Runs J, K and L there was no ethylene consumption until the second quantity of alkyl metal was pressured into the reactor. Run L shows that $EtAlCl_2$ (EADC) is not able to activate $ZrCl_4$, although it is effective with $TiCl_4$, $VCl_4$ and some other Ziegler transition metal catalysts. Thus, one cannot extrapolate the broad disclosures of Ziegler-type cocatalysts for polyethylene to the process of ethylene oligomerization to make linear alpha olefins and waxes.

In Runs J and K, BuLi and $Bu_2Mg$ made small amounts of alpha olefins and in Run M, $AlEt_3$ made alpha olefins at a high rate. However, in all cases, the polyethylene make was unacceptable and caused severe reactor fouling. The oligomer product was too low molecular weight to be useful in a wax process (see Example 2 for discussion) even though the most favorable conditions were used (cocatalyst/catalyst mole ratio less than 1).

The results in these control runs are in sharp contrast to the unexpected outstanding results obtained with dialkyl zinc cocatalyst in Example 1 and 2.

EXAMPLE 4

The procedure of Example 2 was followed except that the $Et_2Zn$ and $ZrCl_4$ were mixed in 1 ml. n-$C_7$ and ground in a Wig-L-Bug (trademark) dental amalgam shaker for 2 minutes and the total slurry was rinsed into the funnel containing solvent.

TABLE IV

| Run | Et$_2$Zn mmol | ZrCl$_4$ mmole | Zn/Zr | Time min. | Rate | $\overline{M}_n$ | % Purity |
| --- | --- | --- | --- | --- | --- | --- | --- |
| N | 0.08 | 0.16 | 0.50 | 30 | 5500 | 265 | 99.6 |
| O | 0.08 | 0.30 | 0.167 | 30 | 11500 | 295 | 98.9 |

Comparison with Runs E and F, Example 2, shows that grinding the catalyst components in the presence of n-heptane increased activity with little effect on molecular weight. The higher $\overline{M}_n$ in Run O versus F is consistent with a slightly lower Zn/Zr ratio.

EXAMPLE 5

The procedure of Example 4 was followed except that after grinding 2 minutes, the catalyst slurry was filtered on a fine glass frit, washed with 20 ml. n-heptane and the solids were transferred as quantitatively as possible to the solvent funnel. No additional cocatalyst was used.

TABLE V

| Run | Et$_2$Zn mmol | ZrCl$_4$ mmole | Zn/Zr | Time min. | Rate | $\overline{M}_n$ | % Purity |
| --- | --- | --- | --- | --- | --- | --- | --- |
| P | 0.10 | 0.10 | 1.0 | 30 | 2600 | 295 | — |
| Q | 0.08 | 0.16 | 0.50 | 30 | 3510 | 271 | 99.3 |
| R | 0.08 | 0.32 | 0.25 | 30 | 2100 | 300 | 99.2 |

Comparison with Runs D, E, F, N, and O shows that lower activity was obtained due to incomplete transfer of catalyst after filtration and to the effect of poisons in the absence of excess alkyl metal scavenger. However, the molecular weight increased significantly, especially at the higher Zn/Zr ratios, and there was no longer a large effect of cocatalyst/catalyst ratio. Thus, after alkylating the zirconium, removal of excess alkyl metal cocatalyst and/or the reaction products from alkylation increased molecular weight and decreased sensitivity to the catalyst proportions.

EXAMPLE 6

The procedure of Example 2 was followed except that the ZrCl$_4$ was premixed 5 minutes at 25° C. with an equimolar amount of hexamethylbenzene (C$_6$Me$_6$), a pi base, in 20 ml. n-heptane. Et$_2$Zn was then added and the mixture stirred 5 minutes before charging to the solvent funnel.

TABLE VI

| Run | Et$_2$Zn mmol | ZrCl$_4$ —C$_6$Me$_6$ mmole | Zn/Zr | Time min. | Rate | $\overline{M}_n$ | % Purity |
| --- | --- | --- | --- | --- | --- | --- | --- |
| S | 0.10 | 0.20 | 0.50 | 15 | 9500 | 261 | 99.5 |
| T | 0.05 | 0.30 | 0.167 | 30 | trace | — | — |
|   | +0.05 |   | 0.333 | 10 | 14700 | 308 | 99.1 |

A comparison with Runs E and F shows that premixing the ZrCl$_4$ with the pi base increased polymerization rate while maintaining high molecular weight.

In contrast, the addition of strong Lewis bases, such as triethylamine or tetrahydrofuran, in amounts only equal to that of the Et$_2$Zn destroyed activity almost completely.

What is claimed is:

1. A process for preparing linear alpha olefins and waxes having a total product $\overline{M}_n$ in the range 200 to 700 which comprises polymerizing an ethylene-containing gas in the presence of the reaction product of a Zr metal compound having the formula ZrX$_a$A$_b$ wherein a=3 or 4, b=0 or 1 and a+b=4 and X=Cl or Br and A is Cl, Br, I, OR or OOCR with R$_2$Zn, wherein R is an alkyl group having about 1 to about 5 carbon atoms in the presence of a diluent at a temperature of about 50° to 200° C. and an ethylene pressure above about 3.5 MPa, wherein the $\overline{M}_n$ of said reaction product is controlled by the molar ratio of said R$_2$Zn/ZrCl$_4$, said molar ratio being about 0.1/1 to about 1/1.

2. A process according to claim 1, wherein said molar ratio is less than 0.5.

3. A process according to claim 1, wherein said R$_2$Zn is Et$_2$Zn.

4. A process according to claim 1 wherein said temperature is about 100° to about 150° C.

5. A process according to claim 2 or 3 wherein said ethylene pressure is at least 5.5 MPa.

6. A process according to claim 1 wherein the $\overline{M}_n$ of said reaction product is >250.

7. A process according to claim 1 in which a pi base is present as a catalyst modifier.

* * * * *